(12) United States Patent
Kuznetsov et al.

(10) Patent No.: US 8,228,374 B2
(45) Date of Patent: Jul. 24, 2012

(54) METHOD TO DETERMINE DIELECTRIC PERMEABILITY OF DIELECTRIC OBJECT

(75) Inventors: Andrey Kuznetsov, St.Petersburg (RU); Igor Gorshkov, St. Petersburg (RU); Valery Averyanov, St. Petersburg (RU)

(73) Assignee: Apstec Systems, Valetta (MT)

( * ) Notice: Subject to any disclaimer, the term of this patent is extended or adjusted under 35 U.S.C. 154(b) by 0 days.

(21) Appl. No.: 13/120,494

(22) PCT Filed: Nov. 24, 2010

(86) PCT No.: PCT/RU2010/000724
§ 371 (c)(1),
(2), (4) Date: Aug. 4, 2011

(87) PCT Pub. No.: WO2011/065868
PCT Pub. Date: Jun. 3, 2011

(65) Prior Publication Data
US 2011/0304698 A1    Dec. 15, 2011

(30) Foreign Application Priority Data
Nov. 26, 2009   (RU) ................. 2009145423

(51) Int. Cl.
*H04N 13/02* (2006.01)
(52) U.S. Cl. ........................................... 348/47
(58) Field of Classification Search ........ 348/47, 348/168; 324/316, 637, 642
See application file for complete search history.

(56) References Cited

U.S. PATENT DOCUMENTS

| 7,040,168 | B1 | 5/2006 | Merkel | |
| 2003/0214309 | A1* | 11/2003 | Shim et al. | 324/637 |
| 2005/0021321 | A1 | 1/2005 | Mochizuki | |
| 2006/0127267 | A1* | 6/2006 | Redko et al. | 419/61 |
| 2007/0293752 | A1* | 12/2007 | Simpkin | 600/407 |
| 2009/0024026 | A9* | 1/2009 | Simpkin | 600/430 |
| 2009/0212789 | A1* | 8/2009 | Lin et al. | 324/642 |
| 2010/0069744 | A1* | 3/2010 | Simpkin | 600/425 |
| 2010/0253783 | A1* | 10/2010 | Furxhi et al. | 348/168 |
| 2011/0057653 | A1* | 3/2011 | Barmatz et al. | 324/316 |
| 2011/0267215 | A1* | 11/2011 | Barr et al. | 342/22 |

FOREIGN PATENT DOCUMENTS

| GB | 2458764 | 10/2009 |
| RU | 2039352 | 7/1995 |
| RU | 2096767 | 11/1997 |
| RU | 2121671 | 11/1998 |

* cited by examiner

*Primary Examiner* — Sath V Perungavoor
*Assistant Examiner* — James Pontius
(74) *Attorney, Agent, or Firm* — Nadya Reingand

(57) ABSTRACT

The invention belongs to the field of electro technique, particularly to the remote determination of dielectric permeability of dielectric objects. The dielectric object at the background of a reflector is radiated by coherent microwave radiation at N-frequencies to produce a three-dimensional (3D) microwave image of the object and reflector. By utilizing multiple cameras a 3D video image is produced, which then is converted into digital format. The 3D video and 3D microwave images are synchronized and then transferred into a general system of coordinates. The dielectric permeability of the object is determined as follows:

Figure 1:
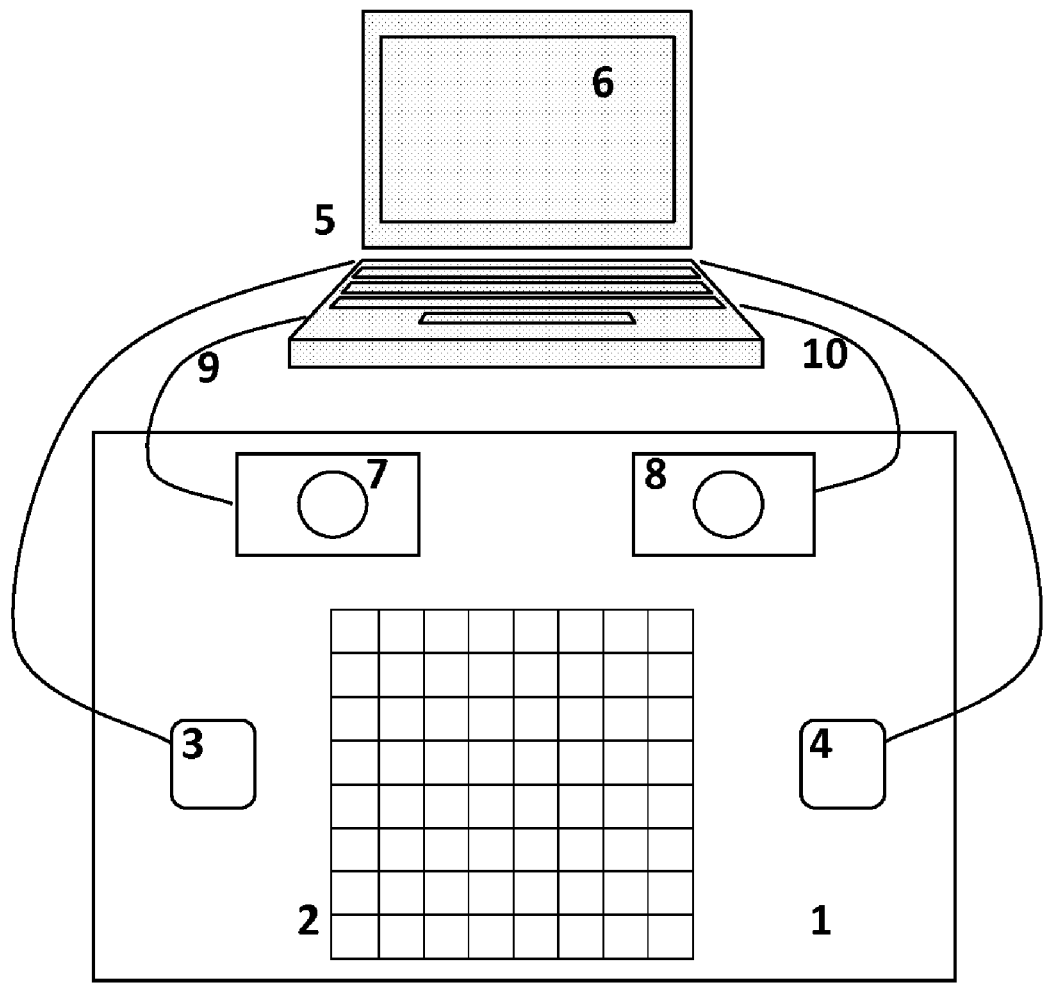
Figure 2:
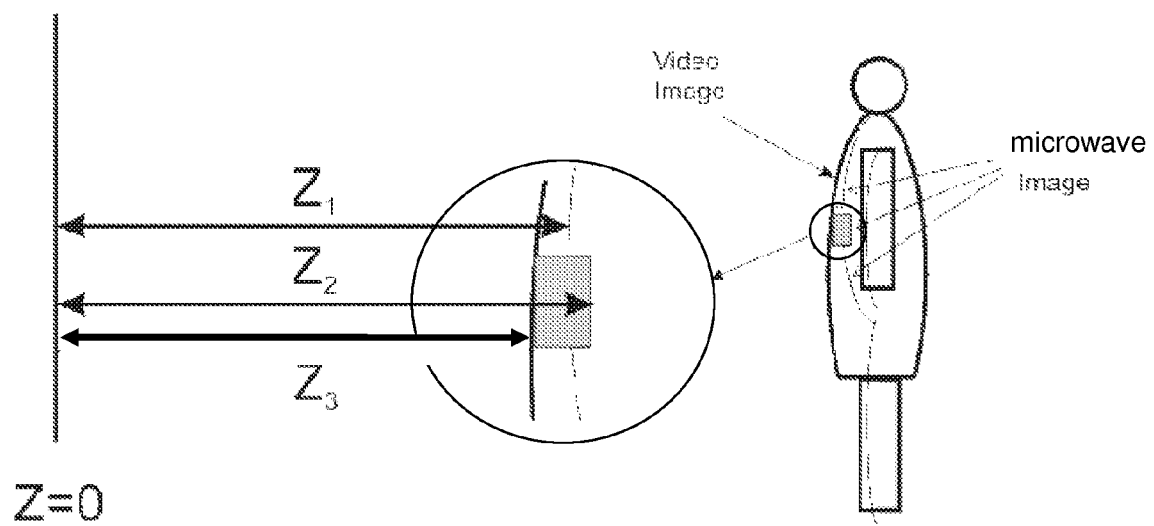

$$\varepsilon = \left(\frac{z_2 - z_3}{z_1 - z_3}\right)^2.$$

where distances $Z_1$ and $Z_2$ are between the source of microwave radiation and the reflector, with and without the dielectric object, respectively, and distance $Z_3$ is between the microwave source and the video image of the dielectric object. This formula allows determining remotely the dielectric permeability of a moving dielectric object of irregular shape.

1 Claim, 2 Drawing Sheets

METHOD TO DETERMINE DIELECTRIC PERMEABILITY OF DIELECTRIC OBJECT

FIELD OF INVENTION

This invention belongs to the field of remote measurement of physical characteristics of the objects, particularly to the remote determination of dielectric permeability of dielectric objects.

BACKGROUND OF THE INVENTION

One of the best-known methods of determining dielectric permeability of the material is to irradiate a sample with an electromagnetic wave using a double-arm emitter. This allows determining the dielectric permeability my measuring the changing difference between the signal's phases in "arms" of the emitter and the measuring length of the passed-through, angled wave. By changing the difference between the signal's phases in "arms" of the emitter, the dependence of the amplitude of the passed-through wave on the length of the "arm" is eliminated. Dielectric permeability can then be derived from the following formula:

$$\varepsilon = \frac{\lambda_0^2}{\operatorname{Sin}^2 Q} \cdot \left(\frac{1}{\Delta} - \frac{1}{\lambda_b}\right)^2,$$

where $\lambda_0$ is free-space wavelength; $\lambda_b$ is length of the wave in double-armed emitter; and $\Delta$ is period of amplitude "zero" the passed-through wave. Angle $\theta$ is chosen according to the ratio $$\left(\frac{d_k}{\lambda_b} - 1\right) < \frac{d_k}{\lambda_0}\sqrt{\varepsilon \operatorname{Sin}\theta} < \left(\frac{d_k}{\lambda_b} + 1\right),$$

where $d_k$ is maximum size of the emitter's "arm", see, for example, USSR Patent No. SU 1800333 A1.

The primary disadvantage of this method is the fact that a contact is required between the emitter and a sample to determine dielectric permeability. Moreover, the sample should have a flat surface to maintain proper contact with the emitter. Thus, this method cannot be used for remote determination of dielectric permeability of the object.

A second method used to determine dielectric permeability of a dielectric object is irradiating the object with coherent microwave radiation at N-frequencies. The microwave radiation is reflected from a background reflector. A border between the object's layers, a boundary between the dielectric object and air, or a physical body, on which the irradiated object is placed, may serve as the reflector. The signal reflected from the dielectric object is then registered. Then it is transferred to the time domain. Peak temporal components in the temporal spectrum are determined and measured. This data is used to calculate the dielectric permeability and the thickness of the layers. Probing and receiving is made into a sector of angles. Dielectric permeability and thickness of layers are then determined from the formulae:

$$\varepsilon_i = \frac{\sqrt{\varepsilon_i}\operatorname{Sin}\theta_{nad1}^{(i)} \cdot c \cdot \left(t_i - \frac{2}{c}\sum_{p=1}^{i-1}\frac{\sqrt{\varepsilon_p}\,\Delta l_p}{\sqrt{1 - \varepsilon_1/\varepsilon_p \cdot \operatorname{Sin}^2\theta_{nad1}^{(i)}}}\right)}{2 \cdot \left(\frac{d}{2} - \sum_{p=1}^{i-1}\Delta l_p \cdot \frac{\varepsilon_1 \operatorname{Sin}\theta_{nad1}}{\sqrt{\varepsilon_p - \varepsilon_1 \operatorname{Sin}^2\theta_{nad1}^{(i)}}}\right)};$$

$$\Delta l_i = \left(t_i - \frac{2}{c}\sum_{p=1}^{i-1}\frac{\sqrt{\varepsilon_{p1}}\cdot\Delta l_p}{\sqrt{1 - \varepsilon_1/\varepsilon_p \cdot \operatorname{Sin}^2\theta_{nad1}^{(i)}}}\right) \cdot \frac{c \cdot \sqrt{1 - \frac{\varepsilon_1}{\varepsilon_i}\operatorname{Sin}^2\theta_{nad1}^{(i)}}}{2\sqrt{\varepsilon_i}},$$

where i is the number of the layer; $\varepsilon_i$ and $\varepsilon_p$ are dielectric permeability of i and p layers; $\varepsilon_1$ is the dielectric permeability of the environment in which probing and receiving of signals is made; $\Delta 1$ is thickness of i-layer;

$$\Delta l = \frac{h_1 + h_2}{2}$$

where $h_1$ and $h_2$ are heights between the border of the first and second layers respectively and points from which probing is made and signal receiving points; $\theta^{(i)}_{nad1}$ is angle of received signal reflected from the border between i and i+1 layer, c is speed of light; $t_1$ is frequency of peak i-constituent of the time spectrum which corresponds with the reflection of the signal from the border between i and i+1 layers, and d is projection of the distance between the point of probing and signal receiving point, see Russian Patent No. RU 2039352.

The main disadvantage of this method, which is taken as a prototype of the proposed invention, is the requirement of parallel arrangement of the layers of the dielectric object. If the object has multiple layers, its sides should be parallel. Due to these requirements this method could be used solely for custom-made objects with required features. This method also requires determined incidence and angles of reflection of the microwave radiation towards the dielectric object.

The aforementioned deems it impossible to use this method for practice in determining dielectric permeability of the moving and hidden object with non-parallel sides or layers, particularly for covert determination of the presence of dielectric explosives hidden on a human body. Dielectric permeability for the most part of such explosives lies between 2.9-3.1.

DETAILED DESCRIPTION

The primary purpose of the proposed invention is to fulfill capability of remote determination of dielectric permeability of the moving dielectric object of irregular shape.

According to the invention of the method of determining dielectric permeability of a dielectric object at the background of the reflector, the dielectric object is radiated by coherent microwave radiation at N-frequencies to produce a three-dimensional microwave image of the dielectric object and the reflector. By using two or more video cameras synchronized with the source of microwave radiation, the produced video image is converted into digital form, and the three-dimensional video image of the specified area is built. The three-dimensional video image and microwave image are transferred into a general system of coordinates; distance $Z_1$ is determined between the source of microwave radiation and the reflector, free of the dielectric object, and distance $Z_2$ is determined between the source of microwave radiation and the section of the microwave image of the reflector in the zone of the dielectric object. By using the video image, distance $Z_3$ is determined between the source of microwave radiation and the video image of the dielectric object, at which point dielectric permeability of the object is determined based on ratio:

$$\varepsilon = \left(\frac{z_2 - z_3}{z_1 - z_3}\right)^2.$$

Realization of this method could be best illustrated through example. To illustrate the method of determining dielectric permeability of the dielectric object at the background of the reflector, a test dummy was used to mimic the human body with the attached dielectric object—beeswax, the dielectric permeability for which should be capable of determining.

The test dummy with the attached dielectric object was radiated with coherent microwave radiation at 14 equidistant frequencies in the range between 8-12 GHz. Irradiation was made using a switched plane antenna array with hexagonal configuration of emitting elements. The array consisted of 256 primary emitters. The reflected signal, in the form of two quadrature components in two parallel receiving channels, was recorded by 12-digit analog-to-digital converters. From these receiving channels, data on the electrical component of the recorded scattered electromagnetic field was transferred onto a PC screen. The microwave image was reconstructed using focusing method (coherent processing). The image was made only for one three-dimensional surface formed with points that have maximal values of intensity in the images of the dielectric object and reflector. Simultaneously, the microwave radiation video image of the dielectric object was received from two digital spatially-separated SDU-415 video cameras. Using this data, the three-dimensional video image of the area with the dielectric object and reflector was obtained.

The microwave image and three-dimensional video image were transferred into a general system of coordinates. In this particular case, the general system of coordinates was set by the antenna array plane and perpendicular intersecting at its center. The microwave image and three-dimensional video image were processed. Value $Z_1$ was determined between the source of microwave radiation and the reflector, free of the dielectric object, and distance $Z_2$ was determined between the source of microwave radiation and the section of the microwave image of the reflector in the zone of the dielectric object. By using the video image, distance $Z_3$ was determined between the source of microwave radiation and the video image of the dielectric object. The dielectric permeability of the object was determined based on the ratio:

$$\varepsilon = \left(\frac{z_2 - z_3}{z_1 - z_3}\right)^2.$$

In our particular example, the distances were the following: $Z_1=122$ cm, $Z_2=128$ cm, $Z_3=112$ cm, and $\varepsilon=2.56$.

Basing the determined value of $\varepsilon$ for the inspected object, one can make a conclusion that the object does not belong to widely spread or commonly used explosive substances, such as TNT, hexogen, tetryl or plastid.

This method could be used for various tasks, for example, to determine the physical characteristics of dielectrics used in electrical industry.

The invention claimed is:

1. A method to determine a dielectric permeability of a dielectric object, comprising:

radiating the dielectric object and a reflector by coherent microwave radiation at N frequencies, wherein the reflector is a surface reflecting back the coherent microwave radiation;

recording signals reflected from the dielectric object and the reflector;

processing the recorded signals by coherent processing to generate microwave images of the dielectric object and the reflector;

creating a three-dimensional microwave image of the dielectric object and the reflector, wherein the three-dimensional microwave image of the dielectric object is created only for one three-dimensional surface formed with points that have maximal values of intensity in the microwave images of the dielectric object and the reflector;

using two video cameras to produce two video images of an area where the dielectric object is located;

digitizing the two video images and producing a digital three-dimensional video image of the area where the dielectric object is located;

synchronizing the three-dimensional video image with the three-dimensional microwave image;

combining the three-dimensional video image and the three-dimensional microwave image in one coordinate system, and;

determining the dielectric permeability of the object $\varepsilon$, using the combined three-dimensional video image and three-dimensional microwave image of the one coordinate system, according to the formula:

$\varepsilon = [(Z_2-Z_3)/(Z_1-Z_3)]^2$, wherein:

$Z_1$ is a distance between a source of microwave radiation and the reflector of the three-dimensional microwave image where the reflector is not covered with the dielectric object, $Z_2$ is a distance between the source of microwave radiation and a section of the reflector of the three-dimensional microwave image where the dielectric object is located, $Z_3$ is a distance between the source of microwave radiation and a section of the three-dimensional video image of the area where the dielectric object is located, and distances $Z_1$, $Z_2$ and $Z_3$ are all distances from the one coordinate system.

* * * * *